(12) United States Patent
Tojo et al.

(10) Patent No.: US 7,919,644 B2
(45) Date of Patent: Apr. 5, 2011

(54) PROCESS FOR PRODUCING AN AROMATIC CARBONATE

(75) Inventors: Masahiro Tojo, Kurashiki (JP);
Hironori Miyaji, Kurashiki (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 782 days.

(21) Appl. No.: 10/593,770

(22) PCT Filed: Jun. 17, 2005

(86) PCT No.: PCT/JP2005/011138
§ 371 (c)(1),
(2), (4) Date: Sep. 22, 2006

(87) PCT Pub. No.: WO2005/123657
PCT Pub. Date: Dec. 29, 2005

(65) Prior Publication Data
US 2007/0185164 A1 Aug. 9, 2007

(30) Foreign Application Priority Data
Jun. 17, 2004 (JP) .................................. 2004-179800

(51) Int. Cl.
*C07C 69/96* (2006.01)
(52) U.S. Cl. ........................................ 558/274
(58) Field of Classification Search .................. 558/274
See application file for complete search history.

(56) References Cited

U.S. PATENT DOCUMENTS

| | | | | |
|---|---|---|---|---|
| 5,210,268 A * | 5/1993 | Fukuoka et al. | ............. | 558/270 |
| 6,262,210 B1 * | 7/2001 | Tojo et al. | ............. | 526/270 |
| 2003/0027941 A1 * | 2/2003 | Sawaki et al. | ............. | 525/461 |
| 2003/0050427 A1 * | 3/2003 | Brunelle et al. | ............. | 528/196 |
| 2003/0088051 A1 * | 5/2003 | Shimoda et al. | ............. | 528/196 |
| 2003/0166826 A1 * | 9/2003 | Miyamoto et al. | ............. | 528/196 |

FOREIGN PATENT DOCUMENTS

| | | |
|---|---|---|
| JP | 51-75044 | 6/1976 |
| JP | 51105032 | 9/1976 |
| JP | 54-48732 A | 4/1979 |
| JP | 54-48733 A | 4/1979 |
| JP | 54-63023 A | 5/1979 |
| JP | 56-25138 A | 3/1981 |
| JP | 56-123948 A | 9/1981 |

(Continued)

OTHER PUBLICATIONS

Gomberg et al. J. Am. Chem. Soc. 1925, 47, 198-211.*

*Primary Examiner* — Joseph R Kosack
*Assistant Examiner* — Matthew P Coughlin
(74) *Attorney, Agent, or Firm* — Birch, Stewart, Kolasch & Birch, LLP

(57) ABSTRACT

A process for producing an aromatic carbonate, which comprises the steps of: (I) transesterifying a starting material selected from the group consisting of a dialkyl carbonate, an alkyl aryl carbonate and a mixture thereof with a reactant selected from the group consisting of an aromatic monohydroxy compound, an alkyl aryl carbonate and a mixture thereof, in the presence of a catalyst, to thereby obtain a high boiling point reaction mixture comprising an aromatic carbonate (a) and an aromatic carbonate ether (b), while withdrawing a low boiling point reaction mixture containing a low boiling point by-product; and (II) separating the aromatic carbonate ether (b) from the high boiling point reaction mixture to thereby obtain a high purity aromatic carbonate.

5 Claims, 2 Drawing Sheets

FOREIGN PATENT DOCUMENTS

| | | |
|---|---|---|
| JP | 56-123949 A | 9/1981 |
| JP | 57-176932 A | 10/1982 |
| JP | 57-183745 A | 11/1982 |
| JP | 58-185536 A | 10/1983 |
| JP | 60-169444 A | 9/1985 |
| JP | 60-169445 A | 9/1985 |
| JP | 60-173016 A | 9/1985 |
| JP | 61-172852 A | 8/1986 |
| JP | 61-291545 A | 12/1986 |
| JP | 62-277345 A | 12/1987 |
| JP | 1-93560 A | 4/1989 |
| JP | 1-265062 A | 10/1989 |
| JP | 1-265063 A | 10/1989 |
| JP | 1-265064 A | 10/1989 |
| JP | 3-291257 A | 12/1991 |
| JP | 4-9358 A | 1/1992 |
| JP | 6-41022 A | 2/1994 |
| JP | 6-157424 A | 6/1994 |
| JP | 6-184058 A | 7/1994 |
| JP | 6-234707 A | 8/1994 |
| JP | 6-263694 A | 9/1994 |
| JP | 6-298700 A | 10/1994 |
| JP | 6-345697 A | 12/1994 |
| JP | 9-176094 A | 7/1997 |
| JP | 11-92429 A | 4/1999 |
| JP | 2003-300936 A | 10/2003 |
| JP | 2004-131421 A | 4/2004 |
| WO | WO-02/40439 A2 | 5/2002 |

* cited by examiner

PROCESS FOR PRODUCING AN AROMATIC CARBONATE

CROSS-REFERENCE TO RELATED APPLICATIONS

This application is the U.S. National Stage Application of International Application No. PCT/JP05/11138, filed Jun. 17, 2005 which claims priority to Japanese Patent Application No. 2004-179800, filed Jun. 17, 2004.

FIELD OF THE INVENTION

The present invention relates to a process for producing an aromatic carbonate. More particularly, the present invention is concerned with a process for producing an aromatic carbonate, which comprises: transesterifying a starting material selected from the group consisting of a dialkyl carbonate, an alkyl aryl carbonate and a mixture thereof with a reactant selected from the group consisting of an aromatic monohydroxy compound, an alkyl aryl carbonate and a mixture thereof, in the presence of a catalyst, to thereby obtain a high boiling point reaction mixture comprising a desired aromatic carbonate (a) and an aromatic carbonate ether (b), while withdrawing a low boiling point reaction mixture containing a low boiling point by-product; and separating the aromatic carbonate ether (b) from the high boiling point reaction mixture to thereby obtain a high purity aromatic carbonate. By the process of the present invention, it becomes possible to produce a high purity aromatic carbonate which exhibits advantageously high reactivity when used as a raw material for a transesterification aromatic polycarbonate.

BACKGROUND OF THE INVENTION

An aromatic carbonate is useful as a raw material for, e.g., the production of an aromatic polycarbonate (whose utility as engineering plastics has been increasing in recent years) without using poisonous phosgene. With respect to the method for the production of an aromatic carbonate, a method for producing an aromatic carbonate or an aromatic carbonate mixture is known, in which a dialkyl carbonate, an alkyl aryl carbonate or a mixture thereof is used as a starting material and an aromatic monohydroxy compound, an alkyl aryl carbonate or a mixture thereof is used as a reactant, and in which a transesterification reaction is performed between the starting material and the reactant, thereby producing an aromatic carbonate or an aromatic carbonate mixture which corresponds to the starting material and the reactant.

However, since this type of transesterification is a reversible reaction in which, moreover, not only is the equilibrium biased toward the original system but the reaction rate is also low, the production of an aromatic carbonate by the above-mentioned method on a commercial scale is accompanied with great difficulties. To improve the above-mentioned method, several proposals have been made, most of which relate to the development of a catalyst for increasing the reaction rate. As a catalyst for use in the method for producing an alkyl aryl carbonate, a diaryl carbonate or a mixture thereof by reacting a dialkyl carbonate with an aromatic hydroxy compound, there have been proposed various metal-containing catalysts, which include for example, a Lewis acid, such as a transition metal halide, or compounds capable of forming a Lewis acid (see, for example, Patent Document 1), a tin compound, such as an organotin alkoxide or an organotin oxide (see, for example, Patent Document 2), salts and alkoxides of an alkali metal or an alkaline earth metal, and lead compounds (see, for example, Patent Document 3), complexes of a metal, such as copper, iron or zirconium (see, for example, Patent Document 4), titanic acid esters (see, for example, Patent Document 5), a mixture of a Lewis acid and a protonic acid (see, for example, Patent Document 6), a compound of Sc, Mo, Mn, Bi, Te or the like (see, for example, Patent Document 7), and ferric acetate (see, for example, Patent Document 8).

As a catalyst for use in the method for producing a diaryl carbonate by a same-species intermolecular transesterification, wherein an alkyl aryl carbonate is disproportionated to a dialkyl carbonate and a diaryl carbonate, there have been proposed various catalysts, which include for example, a Lewis acid and a transition metal compound which is capable of forming a Lewis acid (see, for example, Patent Document 9), a polymeric tin compound (see, for example, Patent Document 10), a compound represented by the formula R—X(=O)OH (wherein X is selected from Sn and Ti, and R is selected from monovalent hydrocarbon groups) (see, for example, Patent Document 11), a mixture of a Lewis acid and a protonic acid (see, for example, Patent Document 12), a lead catalyst (see, for example, Patent Document 13), a titanium or zirconium compound (see, for example, Patent Document 14), a tin compound (see, for example, Patent Document 15), and a compound of Sc, Mo, Mn, Bi, Te or the like (see, for example, Patent Document 7).

Another attempt for improving the yield of aromatic carbonates in these reactions consists in displacing the equilibrium in the direction of the desired product formation as much as possible, by modifying the mode of the reaction process. For example, there have been proposed a method in which by-produced methanol is distilled off together with an azeotrope forming agent by azeotropic distillation in the reaction of a dimethyl carbonate with phenol (see, for example, Patent Document 16), and a method in which by-produced methanol is removed by adsorbing the same onto a molecular sieve (see, for example, Patent Document 17).

Further, a method is known in which an apparatus comprising a reactor having provided on the top thereof a distillation column is employed in order to separate and distill off alcohols (by-produced in the course of the reaction) from a reaction mixture obtained in the reactor (see, for example, Patent Document 18).

As more preferred methods for producing an aromatic carbonate, the present inventors previously developed a method in which a dialkyl carbonate and an aromatic hydroxy compound are continuously fed to a continuous multi-stage distillation column to effect a continuous transesterification reaction in the distillation column, while continuously withdrawing a low boiling point reaction mixture containing a by-produced alcohol from an upper portion of the distillation column by distillation and continuously withdrawing a high boiling point reaction mixture containing a produced alkyl aryl carbonate from a lower portion of the distillation column (see, for example, Patent Document 19), and a method in which an alkyl aryl carbonate is continuously fed to a continuous multi-stage distillation column to effect a continuous transesterification reaction in the distillation column, while continuously withdrawing a low boiling point reaction mixture containing a by-produced dialkyl carbonate by distillation and continuously withdrawing a high boiling point reaction mixture containing a produced diaryl carbonate from a lower portion of the distillation column (see, for example, Patent Document 20). These methods for the first time realized efficient, continuous production of an aromatic carbonate. Thereafter, various methods for continuously producing an aromatic carbonate have further been developed, based on the above-mentioned methods developed by the present inventors. Examples of these methods include a method in which a catalytic transesterification reaction is performed in a column reactor (see, for example, Patent Document 21), a method which uses a plurality of reactors which are connected in series (see, for example, Patent Document 22), a method in which a bubble tower reactor is used (see, for example, Patent Document 23), and a method in which a vertically long reactor vessel is used (see, for example, Patent Document 24).

Also, there have been proposed methods for decreasing the amounts of impurities and/or by-products contained in an aromatic carbonate produced by any of the above-mentioned methods. For example, it is known that when an aromatic carbonate is produced by transesterification, high boiling point substances (each having a boiling point higher than that of the aromatic carbonate) are likely to be by-produced. For example, Patent Document 8/Patent Document 25 discloses that when diphenyl carbonate is produced by a transesterification of dimethyl carbonate with phenol, an impurity having a boiling point equal to or higher than the boiling point of the produced diphenyl carbonate is by-produced, and that the impurity is caused to enter the diphenyl carbonate and causes the discoloration of an ultimate product, such as an aromatic polycarbonate. This prior art document does not disclose an example of the impurity having a boiling point equal to or higher than the boiling point of the produced diphenyl carbonate; however, as an example of the impurity, there can be mentioned an aryloxycarbonyl-(hydroxy)-arene which is produced as an isomer of a diaryl carbonate by Fries rearrangement. More specifically, when diphenyl carbonate is produced as the diaryl carbonate, phenyl salicylate can be mentioned as an example of the aryloxycarbonyl-(hydroxy)-arene. Phenyl salicylate is a high boiling point substance whose boiling point is 4 to 5° C. higher than the boiling point of the diphenyl carbonate.

In this case, when the transesterification is conducted for a long period of time, the above-mentioned high boiling point substance accumulates in the reaction system and the amount of the impurity mixed into the product, namely an aromatic carbonate, tends to increase, so that the purity of the ultimate aromatic carbonate is lowered. Further, as the amount of the high boiling point substance in the reaction mixture increases, the boiling point of the reaction mixture rises, which in turn necessitates the elevation of the temperature of the reaction mixture so as to separate the high boiling point substance. As a result, the by-production of the high boiling point substance is accelerated, thus rendering it difficult to produce a desired aromatic carbonate stably for a prolonged period of time. As a measure for stably producing an aromatic carbonate for a prolonged period of time, there has been proposed a method in which a liquid reaction mixture containing a high boiling point substance and a metal-containing catalyst is withdrawn from the reaction system, followed by reacting the withdrawn reaction mixture with a specific reactant for separating the reaction mixture into a component derived from the high boiling point substance and a component derived from the metal-containing catalyst, thereby removing the high boiling substance from the reaction system (see, for example, Patent Document 26).

Further, impurities and/or by-products having boiling points lower than that of an aromatic carbonate are also known. Specifically, for example, Patent Document 27 proposes a method for separation of alkyl aromatic ethers (anisoles) from an aromatic carbonate.

However, heretofore, there has not been known any method which can be used for efficiently producing a high purity aromatic carbonate which exhibits advantageously high reactivity when used as a raw material for a transesterification aromatic polycarbonate, and, hence, it has been desired to develop such a method.

Patent Document 1: Unexamined Japanese Patent Application Laid-Open Specification No. Sho 51-105032, Unexamined Japanese Patent Application Laid-Open Specification No. Sho 56-123948 and Unexamined Japanese Patent Application Laid-Open Specification No. Sho 56-123949 (corresponding to West German Patent Application Publication No. 2528412, British Patent No. 1499530 and U.S. Pat. No. 4,182, 726)

Patent Document 2: Unexamined Japanese Patent Application Laid-Open Specification No. Sho 54-48733 (corresponding to West German Patent Application Publication No. 2736062), Unexamined Japanese Patent Application Laid-Open Specification No. Sho 54-63023, Unexamined Japanese Patent Application Laid-Open Specification No. Sho 60-169444 (corresponding to U.S. Pat. No. 4,554,110), Unexamined Japanese Patent Application Laid-Open Specification No. Sho 60-169445 (corresponding to U.S. Pat. No. 4,552,704), Unexamined Japanese Patent Application Laid-Open Specification No. Sho 62-277345 and Unexamined Japanese Patent Application Laid-Open Specification No. Hei 1-265063

Patent Document 3: Unexamined Japanese Patent Application Laid-Open Specification No. Sho 57-176932

Patent Document 4: Unexamined Japanese Patent Application Laid-Open Specification No. Sho 57-183745

Patent Document 5: Unexamined Japanese Patent Application Laid-Open Specification No. Sho 58-185536 (corresponding to U.S. Pat. No. 4,410,464)

Patent Document 6: Unexamined Japanese Patent Application Laid-Open Specification No. Sho 60-173016 (corresponding to U.S. Pat. No. 4,609,501)

Patent Document 7: Unexamined Japanese Patent Application Laid-Open Specification No. Hei 1-265064

Patent Document 8: Unexamined Japanese Patent Application Laid-Open Specification No. Sho 61-172852

Patent Document 9: Unexamined Japanese Patent Application Laid-Open Specification No. Sho 51-75044 (corresponding to West German Patent Application Publication No. 2552907 and U.S. Pat. No. 4,045,464)

Patent Document 10: Unexamined Japanese Patent Application Laid-Open Specification No. Sho 60-169444 (corresponding to U.S. Pat. No. 4,554,110)

Patent Document 11: Unexamined Japanese Patent Application Laid-Open Specification No. Sho 60-169445 (corresponding to U.S. Pat. No. 4,552,704)

Patent Document 12: Unexamined Japanese Patent Application Laid-Open Specification No. Sho 60-173016 (corresponding to U.S. Pat. No. 4,609,501)

Patent Document 13: Unexamined Japanese Patent Application Laid-Open Specification No. Hei 1-93560

Patent Document 14: Unexamined Japanese Patent Application Laid-Open Specification No. Hei 1-265062

Patent Document 15: Unexamined Japanese Patent Application Laid-Open Specification No. Hei 1-265063

Patent Document 16: Unexamined Japanese Patent Application Laid-Open Specification No. Sho 54-48732 (corresponding to West German Patent Application Publication No. 2736063 and U.S. Pat. No. 4,252,737)

Patent Document 17: Unexamined Japanese Patent Application Laid-Open Specification No. Sho 58-185536 (corresponding to U.S. Pat. No. 4,410,464)

Patent Document 18: Working examples of Unexamined Japanese Patent Application Laid-Open Specification No. Sho 56-123948 (corresponding to U.S. Pat. No. 4,182,726), Working examples of Unexamined Japanese Patent Application Laid-Open Specification No. Sho 56-25138, Working examples of Unexamined Japanese Patent Application Laid-Open Specification No. Sho 60-169444 (corresponding to U.S. Pat. No. 4,554,110), Working examples of Unexamined Japanese Patent Application Laid-Open Specification No. Sho 60-169445 (corresponding to U.S. Pat. No. 4,552,704), Working examples of Unexamined Japanese Patent Application Laid-Open Specification No. Sho 60-173016 (corresponding to U.S. Pat. No. 4,609,501), Working examples of Unexamined Japanese Patent Application Laid-Open Specification No. Sho 61-172852, Working examples of Unexamined Japanese Patent Application Laid-Open Specification No. Sho 61-291545, and Working examples of Unexamined Japanese Patent Application Laid-Open Specification No. Sho 62-277345

Patent Document 19: Unexamined Japanese Patent Application Laid-Open Specification No. Hei 3-291257

Patent Document 20: Unexamined Japanese Patent Application Laid-Open Specification No. Hei 4-9358

Patent Document 21: Unexamined Japanese Patent Application Laid-Open Specification No. Hei 6-41022, Unexamined Japanese Patent Application Laid-Open Specification No. Hei 6-157424 and Unexamined Japanese Patent Application Laid-Open Specification No. Hei 6-184058

Patent Document 22: Unexamined Japanese Patent Application Laid-Open Specification No. Hei 6-234707 and Unexamined Japanese Patent Application Laid-Open Specification No. Hei 6-263694

Patent Document 23: Unexamined Japanese Patent Application Laid-Open Specification No. Hei 6-298700

Patent Document 24: Unexamined Japanese Patent Application Laid-Open Specification No. Hei 6-345697

Patent Document 25: Unexamined Japanese Patent Application Laid-Open Specification No. Sho 61-172852

Patent Document 26: Unexamined Japanese Patent Application Laid-Open Specification No. Hei 11-92429 (corresponding European Patent No. 1016648 B1)

Patent Document 27: Unexamined Japanese Patent Application Laid-Open Specification No. Hei 9-176094

DISCLOSURE OF THE INVENTION

Problems to Be Solved by the Invention

An object of the present invention is to provide a process for producing a high purity aromatic carbonate which exhibits advantageously high reactivity when used as a raw material for a transesterification aromatic polycarbonate.

Means To Solve The Problems

For solving the above-mentioned problems, the present inventors have made extensive and intensive studies. As a result, they have unexpectedly found that a specific aromatic carbonate ether is contained in an aromatic carbonate produced by a process comprising transesterifying a starting material selected from the group consisting of a dialkyl carbonate, an alkyl aryl carbonate and a mixture thereof with a reactant selected from the group consisting of an aromatic monohydroxy compound, an alkyl aryl carbonate and a mixture thereof, in the presence of a catalyst, to thereby obtain a high boiling point reaction mixture comprising a desired aromatic carbonate, while withdrawing a low boiling point reaction mixture containing a low boiling point by-product. Further, they have also found that, when an aromatic carbonate containing a large amount of the above-mentioned specific aromatic carbonate ether is used as a raw material for producing a transesterification aromatic polycarbonate, the polymerization reactivity of the aromatic carbonate is lowered and the resultant aromatic polycarbonate is discolored, and that, by separating and removing the aromatic carbonate ether from the reaction system for producing an aromatic carbonate to thereby reduce the aromatic carbonate ether content of an aromatic carbonate, it becomes possible to obtain an aromatic carbonate having a high transparency, which exhibits high polymerization reactivity when used as a raw material for an aromatic polycarbonate. The present invention has been completed, based on these novel findings.

The foregoing and other objects, features and advantages of the present invention will be apparent from the following detailed description taken in connection with the accompanying drawings, and the appended claims.

Effects of the Invention

In the aromatic carbonate produced by the process of the present invention, the content of a specific aromatic carbonate ether (which is a conventionally unknown impurity and has a harmful influence on the reactivity of an aromatic carbonate) is reduced. The aromatic carbonate obtained by the process of the present invention has a high purity and exhibits high polymerization reactivity when used as a raw material for an aromatic polycarbonate, so that the aromatic carbonate is useful as a raw material for a transesterification aromatic polycarbonate.

Figure 1:
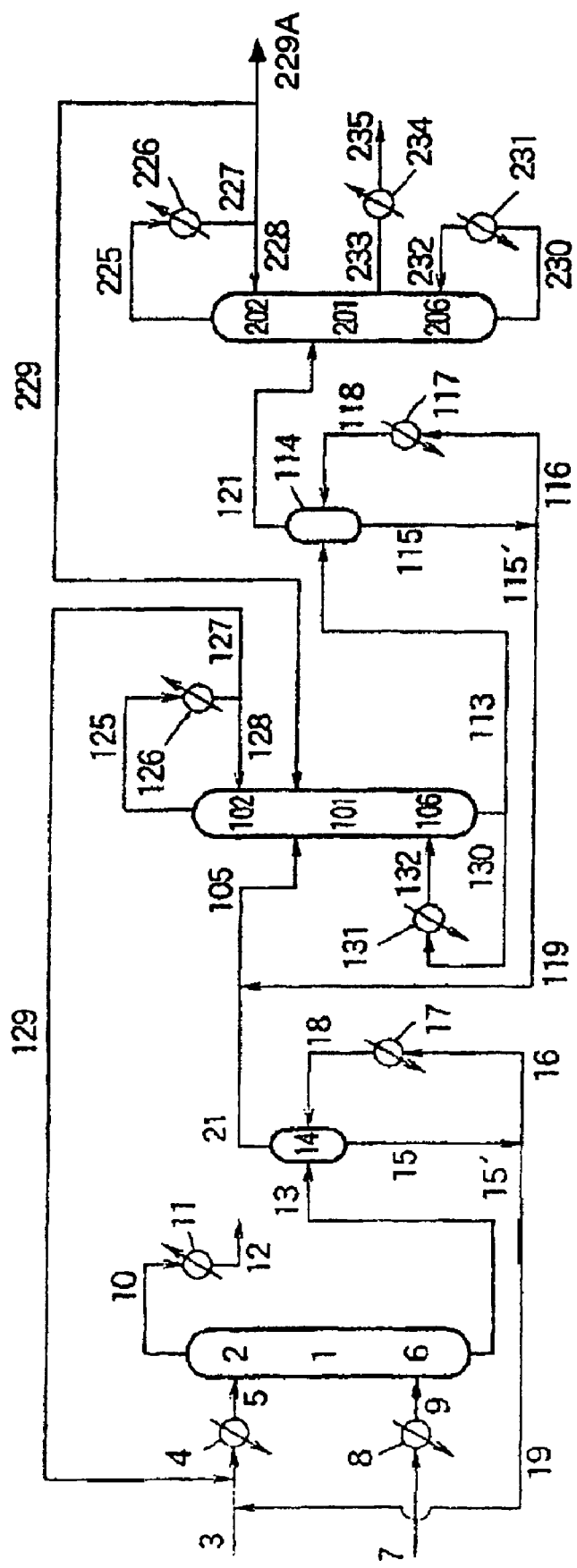
[FIG. 1] A diagram showing a system which is used in the Examples and Comparative Examples.

DESCRIPTION OF REFERENCE NUMERALS 1, 101, 201, 301: continuous multi-stage distillation column
2, 102, 202, 302: top of the continuous multi-stage distillation column
3, 5, 7, 9, 10, 12, 13, 15, 15', 16, 18, 19, 21, 105, 113, 115, 115', 116, 118, 119, 121, 125, 127, 128, 129, 130, 132, 205, 225, 227, 228, 229, 230, 232, 233, 235, 305, 313, 325, 327, 328, 329, 330, 332, 333, 335, 229B, 229C: conduit
4: preheater
6, 106, 206, 306: bottom of the continuous multi-stage distillation column
8: evaporator
11, 126, 226, 234, 326, 334: condenser
14, 114: evaporator
17, 117, 231, 331: reboiler
229A: nozzle

BEST MODE FOR CARRYING OUT THE INVENTION

According to the present invention, there is provided a process for producing an aromatic carbonate, which comprises the steps of:

(I) transesterifying a starting material selected from the group consisting of a dialkyl carbonate represented by the formula (1)

$$R^1OCOOR^1 \quad (1),$$

an alkyl aryl carbonate represented by the formula (2)

$$R^2OCOOAr^2 \quad (2)$$

and a mixture thereof with a reactant selected from the group consisting of an aromatic monohydroxy compound represented by the formula (3)

$$Ar^1OH \quad (3),$$

an alkyl aryl carbonate represented by the formula (4)

$$R^3OCOOAr^3 \quad (4)$$

and a mixture thereof,
wherein each of $R^1$, $R^2$ and $R^3$ independently represents an alkyl group having 1 to 10 carbon atoms, an alicyclic group having 3 to 10 carbon atoms or an aralkyl group having 6 to 10 carbon atoms, and each of $Ar^1$, $Ar^2$ and $Ar^3$ independently represents an aromatic group having 5 to 30 carbon atoms, in the presence of a catalyst, to thereby obtain a high boiling point reaction mixture comprising:
at least one aromatic carbonate (a) which corresponds to the starting material and the reactant and is selected from the group consisting of an alkyl aryl carbonate represented by the formula (5)

$$ROCOOAr \quad (5)$$

and a diaryl carbonate represented by the formula (6)

$$ArOCOOAr \quad (6)$$

wherein R and Ar are, respectively, selected from the group consisting of $R^1$, $R^2$ and $R^3$ and selected from the group consisting of $Ar^1$, $Ar^2$ and $Ar^3$ in correspondence to the starting material and the reactant, and
an aromatic carbonate ether (b) represented by the formula (7)

$$ROR^4OCOOAr \quad (7)$$

wherein R and Ar are as defined above, and $R^4$ is a divalent group $-(CH_2)_m-$, (wherein m is an integer of from 2 to 4) which is unsubstituted or substituted with at least one substituent selected from the group consisting of an alkyl group having 1 to 10 carbon atoms and an aryl group having 6 to 10 carbon atoms, while withdrawing a low boiling point reaction mixture which contains a low boiling point by-product comprising an aliphatic alcohol, a dialkyl carbonate or a mixture thereof corresponding to the starting material and the reactant and represented by at least one formula selected from the group consisting of ROH and ROCOOR, wherein R is as defined above, and (II) separating the aromatic carbonate ether (b) from the high boiling point reaction mixture to thereby obtain a high purity aromatic carbonate.

For easier understanding of the present invention, the essential features and various preferred embodiments of the present invention are enumerated below.

1. A process for producing an aromatic carbonate, which comprises the steps of:
(I) transesterifying a starting material selected from the group consisting of a dialkyl carbonate represented by the formula (1)

$$R^1OCOOR^1 \quad (1),$$

an alkyl aryl carbonate represented by the formula (2)

$$R^2OCOOAr^2 \quad (2)$$

and a mixture thereof with a reactant selected from the group consisting of an aromatic monohydroxy compound represented by the formula (3)

$$Ar^1OH \quad (3),$$

an alkyl aryl carbonate represented by the formula (4)

$$R^3OCOOAr^3 \quad (4)$$

and a mixture thereof,
wherein each of $R^1$, $R^2$ and $R^3$ independently represents an alkyl group having 1 to 10 carbon atoms, an alicyclic group having 3 to 10 carbon atoms or an aralkyl group having 6 to 10 carbon atoms, and each of $Ar^1$, $Ar^2$ and $Ar^3$ independently represents an aromatic group having 5 to 30 carbon atoms, in the presence of a catalyst, to thereby obtain a high boiling point reaction mixture comprising:
at least one aromatic carbonate (a) which corresponds to the starting material and the reactant and is selected from the group consisting of an alkyl aryl carbonate represented by the formula (5)

$$ROCOOAr \quad (5)$$

and a diaryl carbonate represented by the formula (6)

$$ArOCOOAr \quad (6)$$

wherein R and Ar are, respectively, selected from the group consisting of $R^1$, $R^2$ and $R^3$ and selected from the group consisting of $Ar^1$, $Ar^2$ and $Ar^3$ in correspondence to the starting material and the reactant, and
an aromatic carbonate ether (b) represented by the formula (7)

$$ROR^4OCOOAr \quad (7)$$

wherein R and Ar are as defined above, and $R^4$ is a divalent group $-(CH_2)_m-$, (wherein m is an integer of from 2 to 4) which is unsubstituted or substituted with at least one substituent selected from the group consisting of an alkyl group having 1 to 10 carbon atoms and an aryl group having 6 to 10 carbon atoms, while withdrawing a low boiling point reaction mixture which contains a low boiling point by-product comprising an aliphatic alcohol, a dialkyl carbonate or a mixture thereof corresponding to the starting material and the reactant and represented by at least one formula selected from the group consisting of ROH and ROCOOR, wherein R is as defined above, and (II) separating the aromatic carbonate ether (b) from the high boiling point reaction mixture to thereby obtain a high purity aromatic carbonate.

2. The process according to item 1 above, wherein the separation of the aromatic carbonate ether (b) in the step (II) is performed by distillation.

3. The process according to item 1 or 2 above, wherein the step (I) is performed in a continuous manner or each of the steps (I) and (II) is performed in a continuous manner.

4. The process according to item 3 above, wherein the starting material and the reactant are continuously fed to a continuous multi-stage distillation column to perform a transesterification reaction between the starting material and the reactant in a liquid phase or a gas-liquid phase in the presence of a metal-containing catalyst as the catalyst, while continuously withdrawing the high boiling point reaction mixture in a liquid form from a lower portion of the distillation column and continuously withdrawing the low boiling point reaction mixture in a gaseous form from an upper portion of the distillation column, thereby enabling the aromatic carbonate to be produced continuously, wherein the aromatic carbonate ether (b) is separated from the high boiling point reaction mixture withdrawn from the distillation column.

5. The process according to any one of items 1 to 4 above, wherein the content of the aromatic carbonate ether (b) in the high purity aromatic carbonate obtained in the step (II) is not more than 10 ppm by weight.

6. An aromatic carbonate produced by the process of any one of items 1 to 5 above from a starting material selected from the group consisting of a dialkyl carbonate represented by the formula (1)

$$R^1OCOOR^1 \quad (1),$$

an alkyl aryl carbonate represented by the formula (2)

$$R^2OCOOAr^2 \quad (2)$$

and a mixture thereof, and a reactant selected from the group consisting of an aromatic monohydroxy compound represented by the formula (3)

$$Ar^1OH \quad (3),$$

an alkyl aryl carbonate represented by the formula (4)

$$R^3OCOOAr^3 \quad (4)$$

and a mixture thereof, wherein each of $R^1$, $R^2$ and $R^3$ independently represents an alkyl group having 1 to 10 carbon atoms, an alicyclic group having 3 to 10 carbon atoms or an aralkyl group having 6 to 10 carbon atoms, and each of $Ar^1$, $Ar^2$ and $Ar^3$ independently represents an aromatic group having 5 to 30 carbon atoms, the aromatic carbonate containing an aromatic carbonate ether (b) represented by the formula (7)

$$ROR^4OCOOAr \quad (7)$$

wherein R and Ar are, respectively, selected from the group consisting of $R^1$, $R^2$ and $R^3$ and selected from the group consisting of $Ar^1$, $Ar^2$ and $Ar^3$ in correspondence to the starting material and the reactant, and $R^4$ is a divalent group —$(CH_2)_m$— (wherein m is an integer of from 2 to 4) which is unsubstituted or substituted with at least one substituent selected from the group consisting of an alkyl group having 1 to 10 carbon atoms and an aryl group having 6 to 10 carbon atoms, wherein the content of the aromatic carbonate ether (b) in the aromatic carbonate is not more than 10 ppm by weight.

7. An aromatic polycarbonate produced by subjecting an aromatic dihydroxy compound and the aromatic carbonate produced by the process of any one of items 1 to 5 above to a transesterification reaction.

The present invention is described below in detail.

The dialkyl carbonate used as a starting material in the present invention is represented by the following formula (1):

$$R^1OCOOR^1 \quad (1)$$

wherein $R^1$ represents an alkyl group having 1 to 10 carbon atoms, an alicyclic group having 3 to 10 carbon atoms or an aralkyl group having 6 to 10 carbon atoms.

Examples of $R^1$ include alkyl groups, such as methyl, ethyl, propyl (isomers), allyl, butyl (isomers), butenyl (isomers), pentyl (isomers), hexyl (isomers), heptyl (isomers), octyl (isomers), nonyl (isomers), decyl (isomers) and cyclohexylmethyl; alicyclic groups, such as cyclopropyl, cyclobutyl, cyclopentyl, cyclohexyl and cycloheptyl; and aralkyl groups, such as benzyl, phenethyl (isomers), phenylpropyl (isomers), phenylbutyl (isomers) and methylbenzyl (isomers). Each of the above-mentioned alkyl groups, alicyclic groups and aralkyl groups may be substituted with a substituent, such as a lower alkyl group, a lower alkoxy group, a cyano group or a halogen atom, and may also contain an unsaturated bond.

As a dialkyl carbonate having such $R^1$, there may be mentioned dimethyl carbonate, diethyl carbonate, dipropyl carbonate (isomers), diallyl carbonate, di-butenyl carbonate (isomers), dibutyl carbonate (isomers), dipentyl carbonate (isomers), dihexyl carbonate (isomers), diheptyl carbonate (isomers), dioctyl carbonate (isomers), dinonyl carbonate (isomers), didecyl carbonate (isomers), dicyclopentyl carbonate, dicyclohexyl carbonate, dicycloheptyl carbonate, dibenzyl carbonate, diphenethyl carbonate (isomers), di(phenylpropyl)carbonate (isomers), di(phenylbutyl)carbonate (isomers), di(chlorobenzyl)carbonate (isomers), di(methoxybenzyl)carbonate (isomers), di(methoxymethyl)carbonate, di(methoxyethyl)carbonate (isomers), di(chloroethyl)carbonate (isomers) and di(cyanoethyl)carbonate (isomers).

Of these dialkyl carbonates, preferred is a dialkyl carbonate containing, as $R^1$, an alkyl group having 4 or less carbon atoms. More preferred is dimethyl carbonate.

The alkyl aryl carbonate used as the starting material in the present invention is represented by the following formula (2):

$$R^2OCOOAr^2 \quad (2)$$

wherein $R^2$ may be identical with or different from $R^1$, and represents an alkyl group having 1 to 10 carbon atoms, an alicyclic group having 3 to 10 carbon atoms or an aralkyl group having 6 to 10 carbon atoms; and $Ar^2$ represents an aromatic group having 5 to 30 carbon atoms.

As $R^2$, there may be mentioned the same groups as set forth above for $R^1$. Specific examples of $Ar^2$ in formula (2) include: a phenyl group and various alkylphenyl groups, such as phenyl, tolyl (isomers), xylyl (isomers), trimethylphenyl (isomers), tetramethylphenyl (isomers), ethylphenyl (isomers), propylphenyl (isomers), butylphenyl (isomers), diethylphenyl (isomers), methylethylphenyl (isomers), pentylphenyl (isomers), hexylphenyl (isomers) and cyclohexylphenyl (isomers); various alkoxyphenyl groups, such as methoxyphenyl (isomers), ethoxyphenyl (isomers) and butoxyphenyl (isomers); various halogenated phenyl groups, such as fluorophenyl (isomers), chlorophenyl (isomers), bromophenyl (isomers), chloromethylphenyl (isomers) and dichlorophenyl (isomers); various substituted phenyl groups represented by the following formula:

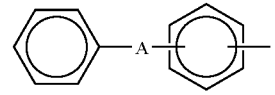

wherein A represents a single bond, a divalent group, such as —O—, —S—, —CO— or —SO$_2$—, an alkylene group or a substituted alkylene group represented by the following formula:

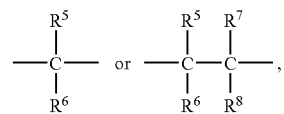

wherein each of $R^5$, $R^6$, $R^7$ and $R^8$ independently represents a hydrogen atom, a lower alkyl group having 1 to 10 carbon atoms, a cycloalkyl group having 3 to 10 carbon atoms, an aryl group having 6 to 10 carbon atoms, or an aralkyl group having 6 to 10 carbon atoms, wherein each of the lower alkyl group, the cycloalkyl group, the aryl group and the aralkyl group may be substituted with a halogen atom or an alkoxy group having 1 to 10 carbon atoms, or a cycloalkylene group represented by the following formula:

wherein k is an integer of from 3 to 11, and each of the hydrogen atoms may be replaced by a lower alkyl group, an aryl group, a halogen atom or the like, and wherein the aromatic ring may be substituted with a substituent, such as a lower alkyl group, a lower alkoxy group, an ester group, a hydroxyl group, a nitro group, a halogen atom or a cyano group;

a naphthyl group and various substituted naphthyl groups, such as naphthyl (isomers), methylnaphthyl (isomers), dimethylnaphthyl (isomers), chloronaphthyl (isomers), methoxynaphthyl (isomers) and cyanonaphthyl (isomers); and various unsubstituted or substituted heteroaromatic groups, such as pyridyl (isomers), cumaryl (isomers), quinolyl (isomers), methylpyridyl (isomers), chloropyridyl (isomers), methylcumaryl (isomers) and methylquinolyl (isomers).

Representative examples of alkyl aryl carbonates having these $R^2$ and $Ar^2$ include methyl phenyl carbonate, ethyl phenyl carbonate, propyl phenyl carbonate (isomers), allyl phenyl carbonate, butyl phenyl carbonate (isomers), pentyl phenyl carbonate (isomers), hexyl phenyl carbonate (isomers), heptyl phenyl carbonate (isomers), octyl tolyl carbonate (isomers), nonyl ethylphenyl carbonate (isomers), decyl butylphenyl carbonate (isomers), methyl tolyl carbonate (isomers), ethyl tolyl carbonate (isomers), propyl tolyl carbonate (isomers), butyl tolyl carbonate (isomers), allyl tolyl carbonate (isomers), methyl xylyl carbonate (isomers), methyl trimethylphenyl carbonate (isomers), methyl chlorophenyl carbonate (isomers), methyl nitrophenyl carbonate (isomers), methyl methoxyphenyl carbonate (isomers), methyl cumyl carbonate (isomers), methyl naphthyl carbonate (isomers), methylpyridyl carbonate (isomers), ethyl cumyl carbonate (isomers), methyl benzoylphenyl carbonate (isomers), ethyl xylyl carbonate (isomers) and benzyl xylyl carbonate.

Of these alkyl aryl carbonates, preferred is an alkyl aryl carbonate which contains, as $R^2$, an alkyl group having 1 to 4 carbon atoms and, as $Ar^2$, an aromatic group having 6 to 10 carbon atoms. More preferred is methyl phenyl carbonate. The starting material used in the present invention is selected from the group consisting of a dialkyl carbonate represented by formula (1) above, an alkyl aryl carbonate represented by formula (2) above and a mixture thereof.

The aromatic monohydroxy compound used as the reactant in the present invention is represented by the following formula (3):

Ar$^1$OH (3)

wherein Ar$^1$ represents an aromatic group having 5 to 30 carbon atoms.

As Ar$^1$, there may be mentioned the same groups as set forth above for Ar$^2$.

Examples of aromatic monohydroxy compounds having such Ar$^1$ include phenol and various alkylphenols, such as phenol, cresol (isomers), xylenol (isomers), trimethylphenol (isomers), tetramethylphenol (isomers), ethylphenol (isomers), propylphenol (isomers), butylphenol (isomers), diethylphenol (isomers), methylethylphenol (isomers), methylpropylphenol (isomers), dipropylphenol (isomers), methylbutylphenol (isomers), pentylphenol (isomers), hexylphenol (isomers) and cyclohexylphenol (isomers); various alkoxyphenols, such as methoxyphenol (isomers) and ethoxyphenol (isomers); various substituted phenols represented by the following formula:

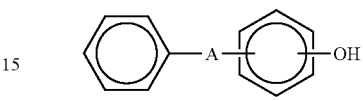

wherein A is as defined above; naphthol (isomers) and various substituted naphthols; and heteroaromatic monohydroxy compounds, such as hydroxypyridine (isomers), hydroxycumarine (isomers) and hydroxyquinoline (isomers).

Of these aromatic monohydroxy compounds, preferred is an aromatic monohydroxy compound containing, as Ar$^1$, an aromatic group having 6 to 10 carbon atoms. More preferred is phenol.

The alkyl aryl carbonate used as the reactant in the present invention is represented by the following formula (4):

R$^3$OCOOAr$^3$ (4)

wherein R$^3$ may be identical with or different from R$^1$ and R$^2$, and represents an alkyl group having 1 to 10 carbon atoms, an alicyclic group having 3 to 10 carbon atoms or an aralkyl group having 6 to 10 carbon atoms; and Ar$^3$ may be identical with or different from Ar$^1$ and Ar$^2$, and represents an aromatic group having 5 to 30 carbon atoms.

As R$^3$, there may be mentioned the same groups as set forth above for R$^1$. As Ar$^3$, there may be mentioned the same groups as set forth above for Ar$^2$.

As alkyl aryl carbonates having these R$^3$ and Ar$^3$, there may be mentioned those which are set forth above for the alkyl aryl carbonates represented by the above-mentioned formula (2). Of these alkyl aryl carbonates, preferred is an alkyl aryl carbonate which contains, as R$^3$, an alkyl group having 1 to 4 carbon atoms and, as Ar$^3$, an aromatic group having 6 to 10 carbon atoms. More preferred is methyl phenyl carbonate.

The reactant used in the present invention is selected from the group consisting of an aromatic monohydroxy compound represented by formula (3) above, an alkyl aryl carbonate represented by formula (4) above and a mixture thereof. The typical reactions, which are involved in the process of the present invention for producing an aromatic carbonate by transesterifying a starting material with a reactant in the presence of a catalyst, are represented by the following formulae (E1), (E2), (E3) and (E4):

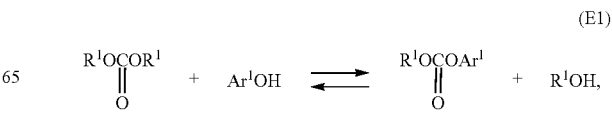

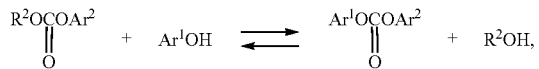

(E2)

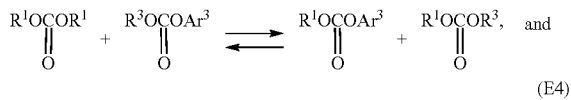

(E3)

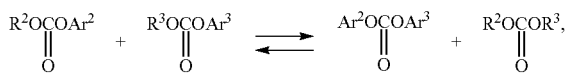

(E4)

wherein $R^1$, $R^2$, $R^3$, $Ar^1$, $Ar^2$ and $Ar^3$ are as defined above, and wherein when $R^2=R^3$ and $Ar^2=Ar^3$ in formula (E4), the reaction is a same-species intermolecular transesterification reaction generally known as a disproportionation reaction.

When each of the reactions of formulae (E1), (E2), (E3) and (E4) is performed according to the process of the present invention, dialkyl carbonates or alkyl aryl carbonates as the starting materials for the reaction can be used individually or in combination and aromatic monohydroxy compounds or alkyl aryl carbonates as the reactants for the reaction can be used individually or in combination.

When $R^2=R^3$ and $Ar^2=Ar^3$ in the transesterification reaction of formula (E4), a diaryl carbonate and a dialkyl carbonate can be obtained by a same-species intermolecular transesterification reaction of a single type of alkyl aryl carbonate. This is a preferred embodiment of the present invention. Further, when $R^1=R^2=R^3$ and $Ar^1=Ar^2=Ar^3$ in formulae (E1) and (E4), by combining the reaction of formula (E1) with the reaction of formula (E4), a diaryl carbonate can be obtained from a dialkyl carbonate and an aromatic monohydroxy compound through an alkyl aryl carbonate as shown in formulae (E5) and (E6) shown below.

(E5)

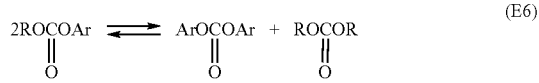

(E6)

The above-mentioned combination is an especially preferred embodiment of the present invention.

Recycling of the dialkyl carbonate by-produced in the reaction of formula (E6) as the starting material for the reaction of formula (E5) results in the formation of 1 mol of a diaryl carbonate and 2 mol of an aliphatic alcohol from 1 mol of a dialkyl carbonate and 2 mol of an aromatic monohydroxy compound. When $R=CH_3$ and $Ar=C_6H_5$ in the above formula (E5), diphenyl carbonate, which is an important raw material for a polycarbonate and a polyisocyanate, can be readily obtained from dimethyl carbonate, which is the simplest form of a dialkyl carbonate, and phenol. This is especially important.

As a catalyst used in the present invention, there can be mentioned any conventional catalyst which is employed for the transesterification reaction occurring in the process of the present invention. Examples of catalysts used in the present invention include metal-containing catalysts.

The metal-containing catalyst used in the present invention is one capable of promoting the reactions of formulae (E1) to (E4). As such metal-containing catalysts, there may be mentioned for example:

<lead compounds> lead oxides, such as PbO, $PbO_2$ and $Pb_3O_4$; lead sulfides, such as PbS and $Pb_2S$; lead hydroxides, such as $Pb(OH)_2$ and $Pb_2O_2(OH)_2$; plumbites, such as $Na_2PbO_2$, $K_2PbO_2$, $NaHPbO_2$ and $KHPbO_2$; plumbates, such as $Na_2PbO_3$, $Na_2H_2PbO_4$, $K_2PbO_3$, $K_2[Pb(OH)_6]$, $K_4PbO_4$, $Ca_2PbO_4$ and $CaPbO_3$; lead carbonates and basic salts thereof, such as $PbCO_3$ and $2PbCO_3 \cdot Pb(OH)_2$; lead salts of organic acids, and carbonates and basic salts thereof, such as $Pb(OCOCH_3)_2$, $Pb(OCOCH_3)_4$ and $Pb(OCOCH_3)_2 \cdot PbO \cdot 3H_2O$; organolead compounds, such as $Bu_4Pb$, $Ph_4Pb$, $Bu_3PbCl$, $Ph_3PbBr$, $Ph_3Pb$ (or $Ph_6Pb_2$), $Bu_3PbOH$ and $Ph_3PbO$ wherein Bu represents a butyl group and Ph represents a phenyl group; alkoxylead compounds and aryloxylead compounds, such as $Pb(OCH_3)_2$, $(CH_3O)Pb(OPh)$ and $Pb(OPh)_2$; lead alloys, such as Pb—Na, Pb—Ca, Pb—Ba, Pb—Sn and Pb—Sb; lead minerals, such as galena and zinc blende; and hydrates of these lead compounds; <copper family metal compounds> salts or complexes of copper family metals, such as CuCl, $CuCl_2$, CuBr, $CuBr_2$, CuI, $CuI_2$, $Cu(OAc)_2$, $Cu(acac)_2$, copper oleate, $Bu_2Cu$, $(CH_3O)_2Cu$, $AgNO_3$, AgBr, silver picrate, $AgC_6H_6ClO_4$, $[AuC\equiv C—C(CH_3)_3]_n$ and $[Cu(C_7H_8)Cl]_4$ wherein acac represents an acetylacetone chelate ligand; <alkali metal complexes> alkali metal complexes, such as Li(acac) and $LiN(C_4H_9)_2$; <zinc complexes> zinc complexes, such as $Zn(acac)_2$; <cadmium complexes> cadmium complexes, such as $Cd(acac)_2$; <iron family metal compounds> iron family metal complexes, such as $Fe(C_{10}H_8)(CO)_5$, $Fe(CO)_5$, $Fe(C_4H_6)(CO)_3$, Co(mesitylene)$_2(PEt_2Ph)_2$, $COC_5F_5(CO)_7$, Ni-$\pi$-$C_5H_5NO$ and ferrocene; <zirconium complexes> zirconium complexes, such as $Zr(acac)_4$ and zirconocene; <Lewis acid compounds> Lewis acids and Lewis acid-forming transition metal compounds, such as $AlX_3$, $TiX_3$, $TiX_4$, $VOX_3$, $VX_5$, $ZnX_2$, $FeX_3$ and $SnX_4$ wherein X represents a halogen atom, an acetoxy group, an alkoxy group or an aryloxy group; and <organotin compounds> organotin compounds, such as $(CH_3)_3SnOCOCH_3$, $(C_2H_5)_3SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(OCH_3)_2$, $(C_2H_5)_3SnOH$, $Ph_3SnOH$, $Bu_2SnO$, $(C_8H_{17})_2SnO$, $Bu_2SnCl_2$ and $BuSnO(OH)$ These catalysts are effective even when they are reacted with an organic compound present in the reaction system, such as an aliphatic alcohol, an aromatic monohydroxy compound, an alkyl aryl carbonate, a diaryl carbonate or a dialkyl carbonate. Those which are obtained by heat-treating these catalysts together with a starting material, a reactant and/or a reaction product thereof prior to the use in the process of the present invention can also be used.

It is preferred that the metal-containing catalyst has high solubility in the liquid phase of the reaction system. Preferred examples of metal-containing catalysts include Pb compounds, such as PbO, $Pb(OH)_2$ and $Pb(OPh)_2$; Ti compounds, such as $TiCl_4$ and $Ti(OPh)_4$; Sn compounds, such as $SnCl_4$, $Sn(OPh)_4$, $Bu_2SnO$ and $Bu_2Sn(OPh)_2$; Fe compounds, such as $FeCl_3$, $Fe(OH)_3$ and $Fe(OPh)_3$; and those products which are obtained by treating the above metal compounds with phenol or a liquid phase of the reaction system.

The transesterification reaction performed in the process of the present invention is an equilibrium reaction. Therefore, in the process of the present invention, in order to displace the equilibrium of the transesterification reaction in the direction of the desired product formation, the transesterification reaction is performed, while withdrawing a low boiling point reaction mixture which contains a low boiling point by-product comprising an aliphatic alcohol, a dialkyl carbonate or a mixture thereof corresponding to the starting material and the reactant and represented by at least one formula selected from the group consisting of ROH and ROCOOR, wherein R is as defined above.

There is no particular limitation with respect to the type of the reactor to be used in the process of the present invention, and various types of conventional reactors, such as a stirred tank reactor, a multi-stage stirred tank reactor and a multi-stage distillation column, can be used. These types of reactors can be used individually or in combination, and may be used either in a batchwise process or a continuous process. From the viewpoint of efficiently displacing the equilibrium in the direction of the desired product formation, a multi-stage distillation column is preferred, and a continuous process using a multi-stage distillation column is especially preferred. There is no particular limitation with respect to the multi-stage distillation column to be used in the present invention as long as it is a distillation column having a theoretical number of stages of distillation of two or more and which can be used for performing continuous distillation. Examples of such multi-stage distillation columns include plate type columns using a tray, such as a bubble-cap tray, a sieve tray, a valve tray and a counterflow tray, and packed type columns packed with various packings, such as a Raschig ring, a Lessing ring, a Pall ring, a Berl saddle, an Intalox saddle, a Dixon packing, a McMahon packing, a Heli pack, a Sulzer packing and a Mellapak. In the present invention, any of the columns which are generally used as a multi-stage distillation column can be utilized. Further, a mixed type of plate column and packed column comprising both a plate portion and a portion packed with packings, can also be preferably used.

In one preferred embodiment of the present invention, the starting material and the reactant are continuously fed to a continuous multi-stage distillation column to perform a transesterification reaction between the starting material and the reactant in a liquid phase or a gas-liquid phase in the presence of a metal-containing catalyst as the catalyst, while continuously withdrawing the high boiling point reaction mixture (containing the aromatic carbonate (a) and the aromatic carbonate ether (b) produced by the transesterification reaction) in a liquid form from a lower portion of the distillation column and continuously withdrawing by distillation the low boiling point reaction mixture (containing the low boiling point by-product) in a gaseous form from an upper portion of the distillation column, thereby enabling the aromatic carbonate to be produced continuously. In this case, the aromatic carbonate ether (b) is separated from the high boiling point reaction mixture withdrawn from the distillation column.

The amount of the catalyst used in the present invention varies depending on the type thereof, the types and weight ratio of the starting material and the reactant, the reaction conditions, such as the reaction temperature and the reaction pressure, and the like. Generally, the amount of the catalyst is in the range of from 0.0001 to 30% by weight, based on the total weight of the starting material and the reactant.

The reaction time (or the residence time when the reaction is continuously conducted) for the transesterification reaction in the present invention is not specifically limited, but it is generally in the range of from 0.001 to 50 hours, preferably from 0.01 to 10 hours, more preferably from 0.05 to 5 hours.

The reaction temperature varies depending on the types of the starting material and reactant, but is generally in the range of from 50 to 350° C., preferably from 100 to 280° C. The reaction pressure varies depending on the types of the starting material and reactant and the reaction temperature, and it may be any of a reduced pressure, an atmospheric pressure and a super-atmospheric pressure. However, the reaction pressure is generally in the range of from 0.1 to $2.0 \times 10^7$ Pa.

In the present invention, it is not necessary to use a reaction solvent. However, for the purpose of facilitating the reaction operation, an appropriate inert solvent, such as an ether, an aliphatic hydrocarbon, an aromatic hydrocarbon or a halogenated aromatic hydrocarbon, may be used as a reaction solvent.

The process of the present invention is characterized in that it comprises a step for separating an aromatic carbonate ether (b) represented by the following formula (7):

$$ROR^4OCOOAr \qquad (7)$$

wherein R and Ar are, respectively, selected from the group consisting of $R^1$, $R^2$ and $R^3$ and selected from the group consisting of $Ar^1$, $Ar^2$ and $Ar^3$ in correspondence to the starting material and the reactant, and $R^4$ is a divalent group $—(CH_2)_m—$ (wherein m is an integer of from 2 to 4) which is unsubstituted or substituted with at least one substituent selected from the group consisting of an alkyl group having 1 to 10 carbon atoms and an aryl group having 6 to 10 carbon atoms.

In conventional processes for producing an aromatic carbonate, the presence of the above-mentioned aromatic carbonate ether (b) has not been known. Therefore, needless to say, there has been no conventional knowledge about the influence of the aromatic carbonate ether (b) on the purity of an aromatic carbonate and the transesterification reactivity of an aromatic carbonate.

Illustrative examples of $R^4$ in formula (7) include: $—CH_2CH_2—$, $—CH(CH_3)CH_2—$, $—CH(CH_3)CH(CH_3)—$, $—CHPhCH_2—$, $—CH_2CH_2CH_2—$, $—CH(CH_3)CH_2CH_2—$, $—CH_2CH(CH_3)CH_2—$ and $—CH_2CH_2CH_2CH_2—$.

Specific examples of the above-mentioned aromatic carbonate ethers (b) include: $CH_3OCH_2CH_2OCOOPh$, $CH_3CH_2OCH_2CH_2OCOOPh$, $CH_3OCH(CH_3)CH_2OCOOPh$, $CH_3OCH_2CH_2CH_2OCOOPh$ and $CH_3OCH_2CH_2CH_2CH_2OCOOPh$.

Conceivable reasons for the presence of the aromatic carbonate ethers (b) in the reaction system are as follows.

(A) An aromatic carbonate ether as an impurity is present in raw materials used for producing an aromatic carbonate by transesterification.

(B) A precursor of an aromatic carbonate ether, as an impurity, is present in raw materials used for producing an aromatic carbonate by transesterification, and the precursor is converted into an aromatic carbonate ether in the reaction system. For example, when a dialkyl carbonate as a raw material contains, as an impurity, a compound represented by the following formula (8):

$$ROR^4OCOOR \qquad (8)$$

wherein R and $R^4$ are as described above for formulae (5) and (7), it is considered that this compound is converted into an aromatic carbonate ether (b) by a reaction with an aromatic monohydroxy compound, an alkyl aryl carbonate or a diaryl carbonate.

In the present invention, for the reason of item (B) above, it is preferred that the content of the aromatic carbonate ether precursor of formula (8) in the dialkyl carbonate used as a starting material is low. Specifically, the content of the precursor of formula (8) is preferably in the range of from 0.1 to 1,000 ppm by weight, more preferably from 0.1 to 300 ppm by weight.

In the present invention, the content of the aromatic carbonate ether (b) of formula (7) as an impurity in the obtained high purity aromatic carbonate is generally 30 ppm by weight or less, preferably 10 ppm by weight or less, more preferably 3 ppm by weight or less, still more preferably 1 ppm by weight or less.

In the present invention, the expression "the reaction system" indicates the inner portions of a reactor, a separation-purification apparatus, a heater, a cooler, a conduit and the like which are used in a system for producing the aromatic carbonate.

With respect to the method for separating the aromatic carbonate ether (b) from the high boiling point reaction mixture, any methods can be employed as long as the aromatic carbonate ether (b) can be separated and removed from the reaction system. Examples of such separation methods include a gas phase-condensed phase separation method, such as a gas phase-liquid phase separation method, a gas phase-solid phase separation method or a gas phase-solid/liquid mixed phase separation method; a solid phase-liquid phase separation method, such as sedimentation, centrifugation or filtration; distillation; extraction; and adsorption. Of these, distillation and adsorption are preferred, and the distillation is more preferred.

As specific examples of the method for separating the aromatic carbonate ether (b) in the case where an aromatic carbonate is produced from dimethyl carbonate (DMC) as the dialkyl carbonate and phenol (PhOH) as the aromatic monohydroxy compound using two multi-stage distillation columns (first and second multi-stage distillation columns) which are connected in series, wherein the synthesis of methyl phenyl carbonate (MPC) is performed in the first multi-stage distillation column and the synthesis of diphenyl carbonate (DPC) is performed in the second multi-stage distillation column, there can be mentioned:

method (i) in which, since the aromatic carbonate ether (b) has a boiling point close to that of DMC, a part of DMC (containing the aromatic carbonate ether (b)), which is formed in the DPC synthesis (in which DPC and DMC are produced by the disproportionation of MPC) and is recycled to the DPC synthesis, is withdrawn from the system, method (ii) in which the DMC which is recycled as mentioned above to the DPC synthesis is purified by distillation to thereby remove the aromatic carbonate ether (b) from the DMC prior to the recycling thereof to the DPC synthesis, and method (iii) in which fresh DMC as the starting material used in the MPC synthesis is purified by distillation to thereby remove $CH_3OCH_2CH_2OCOOCH_3$ (an aromatic carbonate ether precursor of formula (8)) from the fresh DMC.

The above-mentioned separation methods can be employed individually, or at least two of such separation methods can be simultaneously or stepwise employed.

With respect to the temperature and pressure for the separation of the aromatic carbonate ether (b), the temperature and pressure can be appropriately determined, taking into consideration the boiling points of the aromatic carbonate ether (b) and other components (such as dimethyl carbonate) present in the reaction system.

In one preferred embodiment of the present invention, a diaryl carbonate obtained by the process of the present invention is used for producing an aromatic polycarbonate by transesterification. When the diaryl carbonate obtained by the process of the present invention is used for producing an aromatic polycarbonate by transesterification, it becomes possible to perform the polymerization reaction at a high polymerization rate. Further, a high quality aromatic polycarbonate which is colorless can be obtained by the transesterification of an aromatic dihydroxy compound with the diaryl carbonate obtained by the process of the present invention.

With respect to the material of an apparatus used for producing the aromatic carbonate, there is no particular limitation. However, stainless steel, glass or the like is generally used as a material of at least the inner walls of the apparatus.

Hereinbelow, the present invention will be described in more detail with reference to the following Examples and Comparative Examples, but they should not be construed as limiting the scope of the present invention.

The metal concentration of a metal-containing catalyst was measured by means of an ICP (inductively coupled plasma emission spectral analyzer). The concentration of an organic matter in a liquid was measured by gas chromatography.

The number average molecular weight of an aromatic polycarbonate was measured by gel permeation chromatography (GPC) (solvent: tetrahydrofuran; column: polystyrene gel), utilizing the molecular weight conversion calibration curve obtained with respect to the standard mono-disperse polystyrene samples, wherein the molecular weight conversion calibration curve is represented by the following formula:

$$M_{PC}=0.3591 M_{PS}^{1.0388}$$

wherein $M_{PC}$ represents the molecular weight of the aromatic polycarbonate and $M_{PS}$ represents the molecular weight of the standard polystyrene.

All of the concentrations are indicated by weight percentages.

EXAMPLE 1

<Preparation of Catalyst>

A mixture of 40 kg of phenol (PhOH) and 8 kg of lead monoxide was heated at 180° C. for 10 hours, thereby performing a reaction. After that period of time, water formed in the resultant reaction mixture was distilled off together with unreacted phenol to thereby obtain catalyst A.

<Production of Aromatic Carbonate>

Using catalyst A, production of diphenyl carbonate was performed using a system as shown in FIG. 1. Continuous multi-stage distillation column 1 was comprised of a plate column having a height of 12 m and a diameter of 8 inches and equipped with 40 sieve trays. A mixture of dimethyl carbonate (which contained 58 ppm by weight of $CH_3OCH_2CH_2OCOOCH_3$, precursor of the aromatic carbonate ether ($CH_3OCH_2CH_2OCOOPh$)), phenol and methyl phenyl carbonate was continuously fed in a liquid form from conduit 3 through preheater 4 and conduit 5 into continuous multi-stage distillation column 1 at a position of 0.5 m below top 2 thereof at a rate of 31 kg/hr, and was allowed to flow down inside multi-stage distillation column 1, thereby performing a reaction. The formulation of the above-mentioned mixture was adjusted so that a liquid in conduit 5 was comprised of 49.9% by weight of dimethyl carbonate (DMC), 44.7% by weight of phenol (PhOH) and 4.9% by weight of methyl phenyl carbonate (MPC), wherein the liquid in conduit 5 was comprised of a liquid in conduit 19 (wherein the liquid in conduit 19 was recovered from evaporator 14), a liquid in conduit 129 (wherein the liquid in conduit 129 was recovered from continuous multi-stage distillation column 101) and the above-mentioned mixture fed from conduit 3. Dimethyl carbonate (which contained 58 ppm by weight of $CH_3OCH_2CH_2OCOOCH_3$, precursor of the aromatic carbonate ether ($CH_3OCH_2CH_2OCOOPh$)) was fed from conduit 7 to evaporator 8, evaporated in evaporator 8, and fed in a gaseous form through conduit 9 to bottom 6 of continuous multi-stage distillation column 1 at a rate of 55 kg/hr. Catalyst A was fed to continuous multi-stage distillation column 1 in such an amount that the Pb concentration of a reaction mixture in conduit 13 became 0.042% by weight, wherein the Pb concentration can be measured using a sample of the reaction mixture withdrawn through a sampling nozzle (not shown) provided on conduit 13.

Continuous multi-stage distillation column 1 was operated under conditions wherein the temperature at the column bottom was 203° C. and the pressure at the column top was $7.4 \times 10^5$ Pa. Continuous multi-stage distillation column 1 was kept warm by means of a heat insulating material and a part of the column was heated by means of a heater (not shown). Gas distilled from column top 2 was led through conduit 10 into condenser 11, in which the gas was condensed. The resultant condensate was continuously withdrawn at a rate of 55 kg/hr through conduit 12. On the other hand, a reaction mixture was continuously withdrawn from column bottom 6 at a rate of 31 kg/hr and led into evaporator 14 through conduit 13. In evaporator 14, a gas and a concentrated liquid containing catalyst A and the like were formed. A part of the concentrated liquid was led into reboiler 17 through conduits 15 and 16 and recycled to evaporator 14 through conduit 18. The remainder of the concentrate in evaporator 14 was recycled at a rate of 1 kg/hr to continuous multi-stage distillation column 1 through conduits 15, 19 and 3. On the other hand, the gas formed in evaporator 14 was fed through conduits 21 and 105 into continuous multi-stage distillation column 101 at a position of 2.0 m below top 102 thereof, which column was comprised of a plate column having a height of 6 m and a diameter of 10 inches and provided with 20 sieve trays, thereby performing a reaction. The formulation of the mixture in conduit 105 was as follows: DMC: 43.1% by weight; PhOH: 24.5% by weight; MPC: 27.1% by weight; and DPC (diphenyl carbonate): 4.5% by weight (the mixture in conduit 105 was comprised of a gas introduced through conduit 21 and a liquid introduced from conduit 119, which was recycled from evaporator 114). Catalyst A was fed to column 101 in such an amount that the Pb concentration of the reaction mixture in conduit 113 became 0.16% by weight, wherein the Pb concentration can be measured using a sample withdrawn from a sampling nozzle (not shown) provided on conduit 113.

Continuous multi-stage distillation column 101 was operated under conditions wherein the temperature at the column bottom was 198° C. and the pressure at the column top was $3.7 \times 10^4$ Pa. Gas distilled from column top 102 was led through conduit 125 to condenser 126, in which the gas was condensed. A part of the resultant condensate was recycled to column top 102 through conduit 128, and the remainder of the condensate was recycled to continuous multi-stage distillation column 1 through conduits 127 and 129, preheater 4 and conduit 5. After the start of the recycling of the condensate to continuous multi-stage distillation column 1 through conduit 129, fresh phenol was fed from conduit 3 so that the mixture in conduit 5 maintained the above-mentioned formulation.

A part of the reaction mixture at bottom 106 of continuous multi-stage distillation column 101 was led into reboiler 131 through conduit 130, and recycled to column bottom 106 through conduit 132, and the remainder of the reaction mixture was led to evaporator 114 through conduit 113 at a rate of 8.8 kg/hr. In evaporator 114, a gas and an evaporation-concentrated liquid containing the catalyst and high boiling point substances were formed. A part of the concentrated liquid was led into reboiler 117 through conduits 115 and 116 and recycled to evaporator 114 through conduit 118. The remainder of the concentrated liquid in evaporator 114 was recycled to continuous multi-stage distillation column 101 through conduits 115, 119 and 105 at a rate of 2 kg/hr.

The gas formed in evaporator 114 was fed through conduit 121 into continuous multi-stage distillation column 201 at a position of 2.0 m below top 202 thereof, which column was comprised of a plate column having a height of 6 m and a diameter of 6 inches and provided with 20 sieve trays. In column 201, diphenyl carbonate was separated from the gas. Continuous multi-stage distillation column 201 was operated under conditions wherein the temperature at the column bottom was 184° C. and the pressure at the column top was $2 \times 10^3$ Pa. Gas distilled from top 202 of the column was led through conduit 225 to condenser 226, in which the gas was condensed. A part of the resultant condensate was recycled to top 202 of the column through conduit 228, another part of the condensate was recycled to continuous multi-stage distillation column 101 through conduits 227 and 229, and the remainder of the condensate was withdrawn through nozzle 229A provided on conduit 229 at a rate of 0.05 kg/hr. A gas was withdrawn from continuous multi-stage distillation column 201 through conduit 233 provided at a position of 4 m below column top 202 and was led to condenser 234, in which the withdrawn gas was condensed. The resultant condensate was withdrawn at a rate of 6.7 kg/hr through conduit 235.

When the operation reached a stationary state, various analyses were performed. As a result, it was found that the condensate withdrawn from nozzle 229A contained 9.2% by weight of an aromatic carbonate ether ($CH_3OCH_2CH_2OCOOPh$), and that the condensate withdrawn from conduit 235 contained 99.99% by weight or more of diphenyl carbonate, wherein the concentration of the aromatic carbonate ether ($CH_3OCH_2CH_2OCOOPh$) in the condensate was 5 ppm by weight.

COMPARATIVE EXAMPLE 1

Diphenyl carbonate was produced in substantially the same manner as in Example 1, except that the withdrawal of the condensate from nozzle 229A was not performed. When the operation reached a stationary state, various analyses were performed. As a result, it was found that the condensate withdrawn from conduit 235 contained 99.90% by weight to less than 99.99% by weight of diphenyl carbonate, wherein the concentration of an aromatic carbonate ether ($CH_3OCH_2CH_2OCOOPh$) in the condensate was 68 ppm by weight. The results of Example 1 and this Comparative Example 1 show that the purity of the diphenyl carbonate obtained is improved when, as in Example 1, a part of a column top reaction mixture containing an aromatic carbonate ether is withdrawn from continuous multi-stage distillation column 201.

EXAMPLE 2

Figure 2:
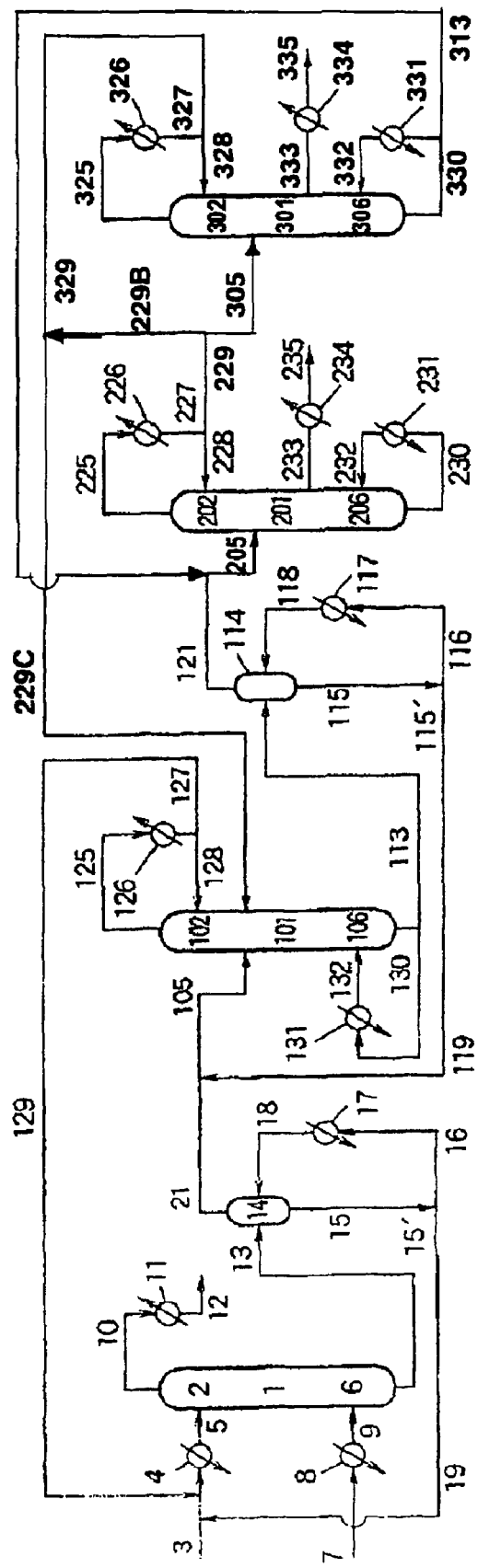
[FIG. 2] A diagram showing another system which is used in the Examples and Comparative Examples.

Diphenyl carbonate was produced in substantially the same manner as in Example 1, except that a system as shown in FIG. 2 was used instead of a system as shown in FIG. 1, and that the following step was further performed: the condensate withdrawn through conduit 229 (wherein the condensate was obtained by condensing the gas withdrawn from the column top of continuous multi-stage distillation column 201) was fed to continuous multi-stage distillation column 301 at a position of 0.8 m below the column top 302 thereof, which column was comprised of a packed column type distillation column having a height of 2 m and a diameter of 2 inches and having packed therein Dixon packings (3 mmϕ). An aromatic carbonate ether was withdrawn from the continuous multi-stage distillation column 301. Continuous multi-stage distillation column 301 was operated under conditions wherein the temperature at the column bottom was 204° C. and the pressure at the column top was $1.5 \times 10^2$ Pa. Gas distilled from column top 302 of the column was led through conduit 325 to condenser 326, in which the gas was condensed. A part of the resultant condensate was recycled to column top 302 of the column through conduit 328, and the remainder of the condensate was recycled to continuous multi-stage distillation column 101 from conduit 229C through conduits 327 and 329 at a rate of 0.05 kg/hr. A gas was withdrawn from continuous multi-stage distillation column 301 through conduit 333 provided at a position of 1.2 m below column top 302 and was led to condenser 334, in which the withdrawn gas was condensed. The resultant condensate was withdrawn at a rate of 0.029 kg/hr through conduit 335.

A part of the reaction mixture at column bottom 306 of continuous multi-stage distillation column 301 was led to reboiler 331 through conduit 330, and recycled to column bottom 306 through conduit 332, and the remainder of the reaction mixture was fed to continuous multi-stage distillation column 201 through conduits 313 and 205 at a rate of 0.021 kg/hr.

When the operation reached a stationary state, various analyses were performed. As a result, it was found that the liquid withdrawn from conduit 335 contained 16% by weight of an aromatic carbonate ether ($CH_3OCH_2CH_2OCOOPh$), and that the condensate withdrawn from conduit 235 contained 99.99% by weight or more of diphenyl carbonate, wherein the aromatic carbonate ether ($CH_3OCH_2CH_2OCOOPh$) was not detected.

COMPARATIVE EXAMPLE 2

Diphenyl carbonate was produced in substantially the same manner as in Example 2, except that the withdrawal of the liquid from conduit 335 was not performed. When the operation reached a stationary state, various analyses were performed. As a result, it was found that the condensate withdrawn from conduit 235 contained 99.90% by weight to less than 99.99% by weight of diphenyl carbonate, wherein the concentration of an aromatic carbonate ether ($CH_3OCH_2CH_2OCOOPh$) in the condensate was 67 ppm by weight. The results of Example 2 and this Comparative Example 2 show that the purity of the diphenyl carbonate obtained is improved when, as in Example 2, the aromatic carbonate ether was withdrawn using continuous multi-stage distillation column 301.

EXAMPLE 3

Diphenyl carbonate was produced in substantially the same manner as in Example 2, except that the rate at which the condensate was withdrawn from conduit 335 was changed to 0.02 kg/hr. When the operation reached a stationary state, various analyses were performed. As a result, it was found that the condensate withdrawn from conduit 235 contained 99.99% or more of diphenyl carbonate, wherein the concentration of the aromatic carbonate ether ($CH_3OCH_2CH_2OCOOPh$) in the condensate was 1 ppm by weight.

EXAMPLE 4

Diphenyl carbonate was produced in substantially the same manner as in Example 2, except that the rate at which the condensate was withdrawn from conduit 335 was changed to 0.015 kg/hr. When the operation reached a stationary state, various analyses were performed. As a result, it was found that the condensate withdrawn from conduit 235 contained 99.99% or more of diphenyl carbonate, wherein the concentration of the aromatic carbonate ether ($CH_3OCH_2CH_2OCOOPh$) was 2.5 ppm by weight.

EXAMPLE 5

235 g of diphenyl carbonate obtained in Example 2 (wherein, in the diphenyl carbonate, the aromatic carbonate ether ($CH_3OCH_2CH_2OCOOPh$) was not detected) and 228 g of bisphenol A were placed in a vacuum reactor equipped with an agitator. The temperature of the resultant mixture was slowly elevated from 180 to 220° C. while stirring and purging the atmosphere of the reactor with nitrogen gas. Subsequently, the reactor was hermetically sealed, and a polymerization was effected under 8,000 Pa for 30 minutes while stirring at 100 rpm and, then, under 4,000 Pa for 90 minutes while stirring at 100 rpm. Thereafter, the temperature of the reactor was elevated to 270° C., and a polymerization was effected under 70 Pa for 1 hour, thereby obtaining an aromatic polycarbonate. The obtained aromatic polycarbonate was colorless and transparent and, hence, had an excellent color. The aromatic polycarbonate had a number average molecular weight of 11,500.

COMPARATIVE EXAMPLE 3

An aromatic polycarbonate was produced in substantially the same manner as in Example 5, except that the diphenyl carbonate (containing 67 ppm by weight of the aromatic carbonate ether ($CH_3OCH_2CH_2OCOOPh$)) obtained in Comparative Example 2 was used. The obtained aromatic polycarbonate was discolored to assume a yellow color, and had a number average molecular weight of 7,500.

EXAMPLE 6

An aromatic polycarbonate was produced in substantially the same manner as in Example 5, except that the diphenyl carbonate (containing 1 ppm by weight of the aromatic carbonate ether ($CH_3OCH_2CH_2OCOOPh$)) obtained in Example 3 was used. The obtained aromatic polycarbonate was colorless and transparent and, hence, had an excellent color. The aromatic polycarbonate had a number average molecular weight of 11,000.

EXAMPLE 7

An aromatic polycarbonate was produced in substantially the same manner as in Example 5, except that the diphenyl carbonate (containing 2.5 ppm by weight of the aromatic carbonate ether ($CH_3OCH_2CH_2OCOOPh$)) obtained in Example 4 was used. The obtained aromatic polycarbonate was colorless and transparent and, hence, had an excellent color. The aromatic polycarbonate had a number average molecular weight of 10,500.

EXAMPLE 8

An aromatic polycarbonate was produced in substantially the same manner as in Example 5, except that the diphenyl carbonate (containing 5 ppm by weight of the aromatic carbonate ether ($CH_3OCH_2CH_2OCOOPh$)) obtained in Example 1 was used. The obtained aromatic polycarbonate was colorless and transparent and, hence, had an excellent color. The aromatic polycarbonate had a number average molecular weight of 9,500.

INDUSTRIAL APPLICABILITY

In the aromatic carbonate produced by the process of the present invention, the content of an aromatic carbonate ether (which is a conventionally unknown impurity and has a harmful influence on the reactivity of an aromatic carbonate) is reduced. The aromatic carbonate obtained by the process of the present invention has a high purity and exhibits high polymerization reactivity when used as a raw material for a polycarbonate, so that the aromatic carbonate is useful as a raw material for a transesterification aromatic polycarbonate.

The invention claimed is:

1. A process for producing an aromatic carbonate, which comprises the steps of:
   (I) transesterifying a starting material selected from the group consisting of a dialkyl carbonate represented by the formula (1)

$$R^1OCOOR^1 \tag{1}$$

an alkyl aryl carbonate represented by the formula (2)

$$R^2OCOOAr^2 \tag{2}$$

and a mixture thereof with a reactant selected from the group consisting of an aromatic monohydroxy compound represented by the formula (3)

$$Ar^1OH \tag{3}$$

an alkyl aryl carbonate represented by the formula (4)

$$R^3OCOOAr^3 \tag{4}$$

and a mixture thereof,
   wherein each of $R^1$, $R^2$ and $R^3$ independently represents an alkyl group having 1 to 10 carbon atoms, an alicyclic group having 3 to 10 carbon atoms or an aralkyl group having 6 to 10 carbon atoms, and each of $Ar^1$, $Ar^2$ and $Ar^3$ independently represents an aromatic group having 5 to 30 carbon atoms,
   in the presence of a catalyst, to thereby obtain a high boiling point reaction mixture comprising:
       at least one aromatic carbonate (a) which corresponds to the starting material and the reactant and is selected from the group consisting of an alkyl aryl carbonate represented by the formula (5)

$$ROCOOAr \tag{5}$$

and a diaryl carbonate represented by the formula (6)

$$ArOCOOAr \tag{6}$$

wherein R and Ar are, respectively, selected from the group consisting of $R^1$, $R^2$ and $R^3$ and selected from the group consisting of $Ar^1$, $Ar^2$ and $Ar^3$ in correspondence to the starting material and the reactant, and
       an aromatic carbonate ether (b) represented by the formula (7)

$$ROR^4OCOOAr \tag{7}$$

wherein R and Ar are as defined above, and $R^4$ is a divalent group $-(CH_2)_m-$ (wherein m is an integer of from 2 to 4) which is unsubstituted or substituted with at least one substituent selected from the group consisting of an alkyl group having 1 to 10 carbon atoms and an aryl group having 6 to 10 carbon atoms,
   while withdrawing a low boiling point reaction mixture which contains a low boiling point by-product comprising an aliphatic alcohol, a dialkyl carbonate or a mixture thereof corresponding to the starting material and the reactant and represented by at least one formula selected from the group consisting of ROH and ROCOOR, wherein R is as defined above, and
   (II) separating said aromatic carbonate ether (b) from said high boiling point reaction mixture to thereby obtain a highly purified aromatic carbonate, wherein the content of said aromatic carbonate ether (b) in said highly purified aromatic carbonate is not more than 10 ppm by weight.

2. The process according to claim 1, wherein the separation of said aromatic carbonate ether (b) in said step (II) is performed by distillation.

3. The process according to claim 1, wherein said step (I) is performed in a continuous manner or each of said steps (I) and (II) is performed in a continuous manner.

4. The process according to claim 3, wherein said starting material and said reactant are continuously fed to a continuous multi-stage distillation column to perform a transesterification reaction between said starting material and said reactant in a liquid phase or a gas-liquid phase in the presence of a metal-containing catalyst as said catalyst, while continuously withdrawing said high boiling point reaction mixture in a liquid form from a lower portion of the distillation column and continuously withdrawing said low boiling point reaction mixture in a gaseous form from an upper portion of the distillation column, thereby enabling the aromatic carbonate to be produced continuously,
   wherein said aromatic carbonate ether (b) is separated from said high boiling point reaction mixture withdrawn from said distillation column.

5. A process for producing an aromatic polycarbonate, which comprises producing an aromatic carbonate by the process of claim 1 and subjecting an aromatic dihydroxy compound and the aromatic carbonate to a transesterification reaction.

* * * * *